US009885681B2

(12) United States Patent
Gundersen

(10) Patent No.: US 9,885,681 B2
(45) Date of Patent: Feb. 6, 2018

(54) APPARATUS AND METHOD FOR CHARACTERIZATION OF FLUIDS OR POWDERS BY ELECTRICAL PERMITTIVITY

(71) Applicant: Advantec Sensing AS, Stord (NO)

(72) Inventor: Tore Gundersen, Rykkin (NO)

(73) Assignee: Advantec Sensing AS, Stord (NO)

(*) Notice: Subject to any disclaimer, the term of this patent is extended or adjusted under 35 U.S.C. 154(b) by 0 days.

(21) Appl. No.: 15/023,350

(22) PCT Filed: Jun. 2, 2014

(86) PCT No.: PCT/NO2014/050088
§ 371 (c)(1),
(2) Date: Mar. 18, 2016

(87) PCT Pub. No.: WO2015/041537
PCT Pub. Date: Mar. 26, 2015

(65) Prior Publication Data
US 2016/0245770 A1    Aug. 25, 2016

(30) Foreign Application Priority Data
Sep. 18, 2013  (NO) .................................... 20131253

(51) Int. Cl.
*G01R 27/26* (2006.01)
*G01R 27/08* (2006.01)
(Continued)

(52) U.S. Cl.
CPC ........... *G01N 27/221* (2013.01); *G01N 27/06* (2013.01); *G01N 27/226* (2013.01); *G01R 27/26* (2013.01); *G01N 33/2823* (2013.01)

(58) Field of Classification Search
CPC .... G01N 27/221; G01N 27/06; G01N 27/226; G01N 33/2823; G01R 27/26
(Continued)

(56) References Cited

U.S. PATENT DOCUMENTS 4,586,108 A    4/1986  Frick
4,987,782 A    1/1991  Shkedi et al.
(Continued)

FOREIGN PATENT DOCUMENTS

NO    327881 B1    5/2000

OTHER PUBLICATIONS

International Search Report dated Feb. 13, 2015, dated PCT/NO2014/050088, filed Jun. 2, 2014 (4 pages).
(Continued)

*Primary Examiner* — Farhana Hoque
(74) *Attorney, Agent, or Firm* — Knobbe, Martens, Olson & Bear, LLP

(57) ABSTRACT

In an embodiment, an apparatus for determining a value of a parameter related to electrical permittivity of a fluid includes capacitor formed by at least one electrode on a first side of a dielectric barrier and at least a part of an electrically conducting housing surrounding the barrier. The housing is adapted for being sealingly attached to a container so as to allow the fluid to be characterized to occupy a space between the housing and a side of the barrier, and an electronic relaxation type oscillator circuit is arranged on a miniature circuit board being fit to the housing and connected with the capacitor. An electrical power supply is connected to supply electrical power to the oscillator at an ultra-stable supply voltage, and a frequency measuring device coupled to the oscillator circuit for providing a measured oscillator frequency representing the electrical permittivity dependent on capacitance and resistance.

20 Claims, 3 Drawing Sheets

(51) Int. Cl.
*G01N 27/22* (2006.01)
*G01N 27/06* (2006.01)
*G01N 33/28* (2006.01)

(58) Field of Classification Search
USPC .................. 324/750.3, 861.04, 663, 698
See application file for complete search history.

(56) References Cited

U.S. PATENT DOCUMENTS

| | | |
|---|---|---|
| 5,459,406 A | 10/1995 | Louge |
| 5,973,503 A | 10/1999 | Kuipers et al. |
| 6,320,393 B1 | 11/2001 | Yasui et al. |
| 2004/0108861 A1 | 6/2004 | Germiquet et al. |
| 2004/0251919 A1* | 12/2004 | Stahlmann ............. G01N 27/06 324/663 |
| 2009/0173165 A1* | 7/2009 | Benestad ................ G01F 1/586 73/861.04 |

OTHER PUBLICATIONS

Reverter, F. et al. Liquid-Level Measurement System Based on a Remote Ground Capacitive Sensor. Sensors and Actuators A. 2007, vol. 138, No. 1, pp. 1-8, ISSN 0924-4247.
Druart, S. et al. "CMOS Test Circuit Architecture for the Extraction of Fluid Properties Using Interdigitated Electrodes and Microsensors." In: 16th International Solid-Sate Sensors, Actuators and Microsystems Conference (Transducers 2011). IEEE, pp. 2398-2401.
Extended European Search report dated Mar. 24, 2017 for European Application No. 14846687.3, in 9 pages.

* cited by examiner

APPARATUS AND METHOD FOR CHARACTERIZATION OF FLUIDS OR POWDERS BY ELECTRICAL PERMITTIVITY

CROSS REFERENCE TO RELATED APPLICATIONS

This application is the U.S. National Phase Application under 35 U.S.C. § 371 of International Application No. PCT/NO2014/050088, filed Jun. 2, 2014, designating the U.S. and published as WO 2015/041537 on Mar. 26, 2015, which claims the benefit of Norwegian Patent Application No. 20131253, filed Sep. 8, 2013, which is hereby incorporated by reference in their entirety.

FIELD OF THE INVENTION

The present invention relates to a method and apparatus for characterization of a fluid media or composition of fluid media by measuring a parameter related to electrical permittivity of the fluid. More particularly, the invention for characterization of a fluid relates to measuring a frequency of oscillation of an electrical relaxation oscillator oscillating at a frequency that is determined by an electrical capacitance of an electrical capacitor adapted for the fluid media or composition of fluid media to form part of a dielectric between two respective capacitor plate forming elements, whereby the electrical capacitance is made dependent on a permittivity of the fluid media or composition of fluid media.

BACKGROUND

A substantial number of commonly used and well known industrial processes involve transporting various media in pipes, and storage or separation of these in tanks or vessels, in particular pressurized tanks or vessels holding media under high pressure and at elevated temperatures. Determination of the type and character of the media contained in the tank or vessel by electronic means is a substantial element for managing and controlling such processes.

In several applications it is of importance that measurements can be made through a wall of a pressurized container. This applies to various industries, such as e.g. to the petroleum industry or the food industry. In the petroleum industry, it will be advantageous to be able to determine the relative composition of water, hydro carbons in various states, and gas using a probe positioned in the interior of a vessel or installed in a pipe wall. Similarly, a plurality of sensor devices according to the invention could advantageously be located at different levels in a tank, pipe, or vessel, to determine the composition of the media contained therein at corresponding levels, such as e.g. in a separator tank for processing and separating the various phases in a multiphase flow from a hydrocarbon well. Thereby, that the level of water, gas, and oil within the tank may be determined on a continuous basis, and without interrupting a process involving the media. Typically, there will be considerable dynamics in a separator container when processing a production stream, such that distinct levels or clear interfaces between the various phases of the media contained in may not be formed. By applying electrical measurements based on a variation of electrical capacitance of an electrical capacitor of which the media in the pressurized container forms at least a part of a dielectric between the plates of the capacitor, the condition that the respective dielectric constant, herein also referred to as the electrical permittivity, of water, oil, and gas phases are widely different from each other is exploited, such that the relative portions of the different phases in a mixture at levels of interest within the container may be inferred.

In known solutions where relative portions of the different phases in a mixture at levels of interest within the container are inferred from electrical measurements based on a variation of electrical capacitance value C of an electrical capacitor as a function of the effective dielectric constant of the media to which the capacitor is exposed, the electrical capacitor of electrical capacitance value C is coupled with an inductive element of electrical inductance value L to form an electrical resonator having a resonance at angular frequency w that generally is generally given by $w=(C*L)^{-1/2}$. The angular frequency w at resonance, which is measured to infer the relative portions of the different phases in the media composition, hence, varies not only proportionally with the square root of the electrical capacitance value C of the electrical capacitor, but also proportionally with the square root of the electrical inductance value L of the inductor. Accordingly, the stability and accuracy of the frequency w to be measured as a function of the capacitance value C of the capacitor that is exposed to the media in the tank or container, greatly depends on the degree to which the inductance value L of the inductor may be controlled and kept stable for a measurement period, and sensitivity of the inductor to stimuli due to mechanical vibration and other environmental conditions that have an effect on the inductance value L of the inductor. In the case of monitoring the processing of a hydrocarbon well stream, or other fluid that is streaming or being pumped to a tank or container, typically at high or rapidly varying velocities, rapidly varying and powerful mechanical impulse and vibration noise is generated and inevitably coupled to the resonator circuit of the sensor, and requires complex or intricate mechanical, electrical and signal processing designs in order for the noise to filtered out or compensated for in the signal for measuring the frequency of the resonator.

Accordingly, there is a need for an improved apparatus and method for measuring a parameter related to electrical permittivity of a fluid or fluid media composition in a container.

The invention is in part enabled by the recent development of semiconductor based miniaturized circuitry, allowing for the provision of an ultra-accurate power supply using commercially available electronic components.

SUMMARY OF THE INVENTION

The invention provides an apparatus for determining a value of a parameter related to electrical permittivity of a fluid media or a composition of fluid media to be characterized in a first container. The apparatus advantageously comprises an electronic sensor comprising a first electrical capacitor formed by at least one electrode on a first side of a dielectric barrier and at least a first part of an electrically conducting housing surrounding at least a circumference part of the dielectric barrier and being sealingly attached thereto, the housing being adapted for being sealingly attached to wall of one of the first container or a second container so as to allow the fluid media or the composition of fluid media to be characterized to occupy a space between the first part of the housing and a second side of the dielectric barrier opposite to the first side, and an electronic relaxation type first oscillator circuit arranged on a first miniature circuit board being fit to the housing and connected with the first electrical capacitor, an electrical power supply connected to the first oscillator circuit and being adapted to supply electrical power to the first oscillator, and a first frequency measuring device coupled to the first oscillator circuit for providing a measured first oscillator frequency representing the electrical permittivity. The first oscillator circuit is arranged to oscillate at the first oscillator frequency dependent on an electrical capacitance of the first electrical capacitor and an electrical resistance of a first electrical resistor. The first oscillator circuit includes an electronic inverter circuit formed by a first integrated advanced high-speed CMOS electronic Schmitt trigger circuit. The electrical power supply is an ultra-stable electrical power supply adapted to supply electrical power to the first oscillator circuit at an ultra-stable supply voltage.

According to a first aspect, the electronic inverter circuit included in the first oscillator circuit an embodiment of the apparatus of the invention is formed by a NAND gate having one gate output connected to a first terminal of the first resistor and at least two gate inputs whereof a first gate input is connected to the electrode of the first capacitor and a second terminal of the first resistor.

In an apparatus of the invention according to the first aspect, a second one of the at least two gate inputs is connected to an electrical control line so as to provide a start/stop input of the first oscillator circuit.

According to second aspect of the apparatus of invention, the electrical resistance of the first electrical resistor is selected for the first oscillator frequency to be in a range from about 2 MHz to 100 MHz.

In an apparatus of the invention according to the second aspect, the electrical resistance of the first electrical resistor is selected for the first oscillator frequency to be in a range from about 10 MHz to 20 MHz.

According to third aspect of the apparatus of invention, the first integrated advanced high-speed CMOS electronic Schmitt trigger circuit is part of a miniature surface mount integrated circuit.

In an apparatus of the invention according to the third aspect, the first integrated advanced high-speed CMOS electronic Schmitt trigger circuit is a monolithic-silicon-on-sapphire integrated circuit.

In an apparatus of the invention according to the third aspect, the first integrated advanced high-speed CMOS electronic Schmitt trigger circuit contains a plurality of integrated advanced high-speed CMOS electronic Schmitt trigger circuits, and a second one of the plurality of integrated advanced high-speed CMOS electronic Schmitt trigger circuits is connected to a temperature stable second electrical capacitor and a temperature sensitive second electrical resistor to form a relaxation type second oscillator circuit being arranged to oscillate at a second oscillator frequency dependent on a temperature stable electrical capacitance of the second electrical capacitor and a temperature dependent electrical resistance of the second electrical resistor, and the apparatus further comprising a second frequency measuring device coupled to the second oscillator circuit for providing a measured second oscillator frequency representing a temperature of the apparatus, and a temperature compensating means adapted to modify the measured first oscillator frequency representing the electrical permittivity in response to the measured second oscillator frequency.

According to a further aspect of the apparatus of invention, the housing is a thick walled, hollow cylindrical housing with a substantially circular cross section, the dielectric barrier is positioned to seal off a first end of the cylindrical housing, the first miniature circuit board is positioned on the second end of the cylindrical housing, and the at least one first electrode being connected to the first oscillator circuit on the first miniature circuit board by a substantially straight electrical conductor positioned centrally in the cylindrical housing.

According to a yet further aspect of the apparatus of invention, the dielectric barrier is a ceramic substrate sealingly brazed at to the housing at the circumference part.

According to the invention, electrical capacitance measurements are made using a capacitive electronic sensor comprising a first electrical capacitor formed by at least one electrode on a ceramic substrate located proximal to a composition of media contained in a pressurized container and an electrically conducting housing surrounding part of the electrode on a ceramic substrate, and an electronic relaxation type oscillator being connected to the first electrical capacitor and arranged to oscillate at a frequency that is dependent on the electrical capacitance of the first electrical capacitor and comprising an integrated electronic Schmitt trigger circuit being fed with electrical power by an ultra-accurate power supply, to provide a stable, reliable, and accurate measurement of a characteristic parameter of the composition of the media.

In an embodiment of the invention, the electronic circuitry forming the electronic oscillator is arranged on a circuit board being attached and located in close proximity to the electrically conducting housing surrounding part of the electrode on a ceramic substrate.

In a further embodiment of the invention, a microprocessor or microcontroller is arranged on the circuit board, in close proximity to the.

The present invention provides a method of providing the apparatus of the invention, and methods of providing the apparatus of the invention according to respective aspects disclosed above.

DETAILED DESCRIPTION OF THE INVENTION

Figure 1:
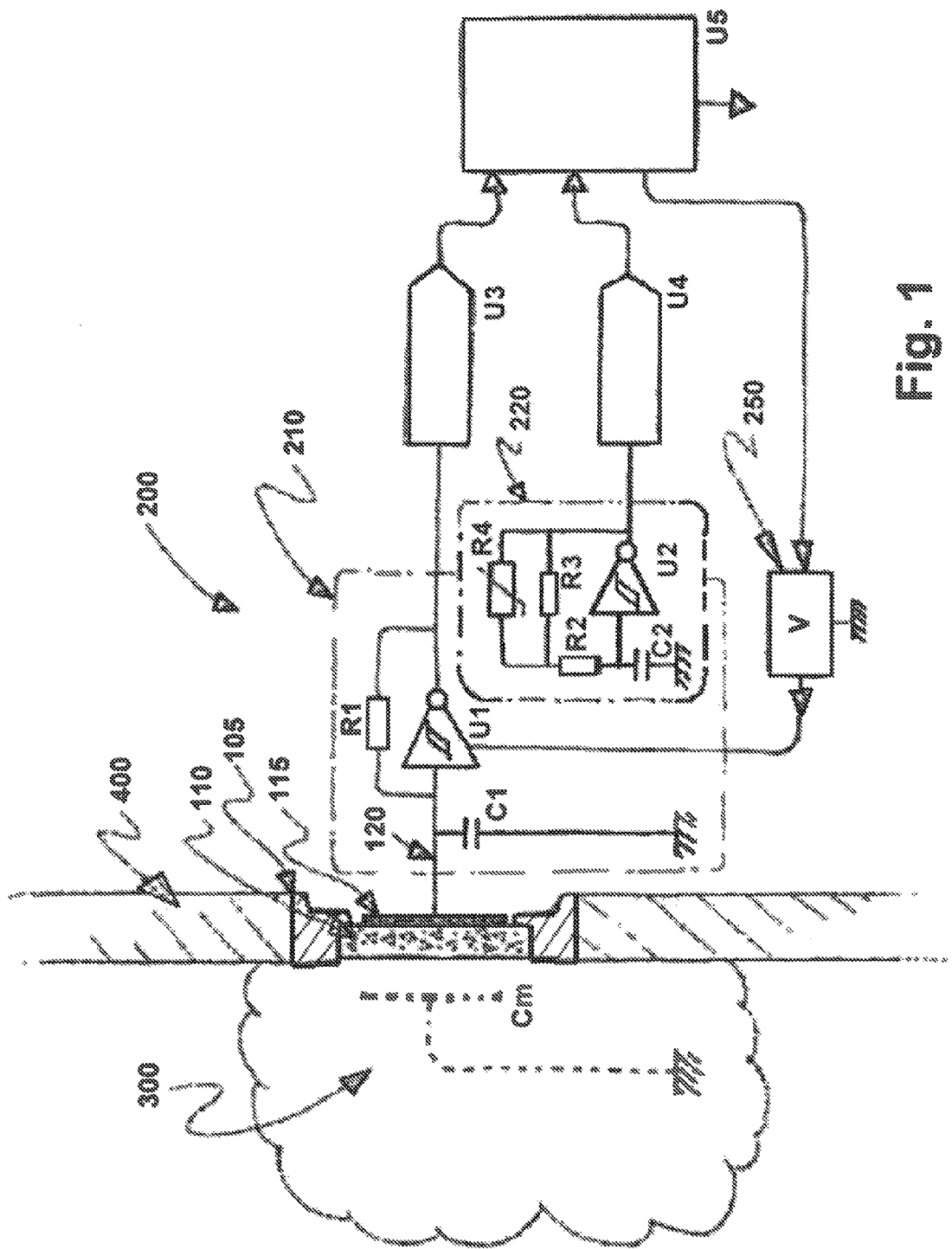
FIG. 1 is a generalized in part circuit schematic and in part block schematic illustration of a sensor device embodiment of the present invention.

In the following, a sensor apparatus according to the present invention is explained by way of exemplary embodiment, first with reference to FIG. 1 which provides a generalized illustration of the sensor and its application, in part in a schematic circuit presentation and in part in a block schematic presentation. With regard to its application, the sensor of the invention is illustrated in a cross section view as being installed in a wall 400 of a pressure carrying pipe or container, with the possibly pressurized medium or media, illustrated by "cloud" 300, to be characterized by the sensor in located to the left of the wall 400 carrying sensor. The term high pressure as referred to in this explanation indicates that the medium 300 held in the container, which could be a tank, a pipe, or other vessel, is at a pressure that is either significantly higher or lower than the pressure of the volume in which other elements of the sensor are located.

Accordingly, the area located to the right of the wall 400 is for convenience referred to as a low pressure area in which at least the electronic circuitry 200 of media dependent oscillator 210 is arranged, optionally, together with a co-located temperature dependent oscillator 220. The sensor generally comprises a wall mounted mechanical sub assembly comprising a cylindrical metal sensor housing 105 sealingly mounted in the wall 400. A window 110 of a pressure resistant solid dielectric material is sealingly attached to the housing, to provide a basis for forming an electric capacitor illustrated by Cm in which the medium 300 also will from part of the dielectric, and to ensure that the medium 300 does not leak from the high pressure side to the low pressure side. Advantageously, the dielectric window is made from a ceramic material, such as e.g. zirconium oxide, that provides high mechanical strength and over a broad temperature range, and a suitable dielectric permittivity. Accordingly, the side of the window facing the high pressure side is generally free, while the side of the window on the low pressure side carries over a large part of the surface an electrode 115 of a material of good electrical conductivity. Thereby an electric capacitor is formed by the electrode 115 and the housing 105. In cases where the wall 400 is of an electrically conducting material, such as e.g. steel or other metal, the wall 400 provides an electrical extension of the housing 105 and serves also to form part of the electrical capacitance illustrated by Cm in which the medium 300 serves as a dielectric together with the dielectric window 110. The electrode 155 has an very short electrical connection 120 to other elements of a highly stable and noise insensitive electronic relaxation oscillator, in particular as the electrical connection 120 is arranged to connect the electrode 155 to the Schmitt trigger input integrated circuit U1 providing an inverting output which is fed back to the input by the resistor R1. Thus, the inverting output of the Schmitt trigger inverter being fed back to its input provides a 180 degree phase shift for astable operation to alternately charge and discharge the capacitor Cm, and the time constant provided by the stable resistance value of resistor R1 and the medium 300 dependent capacitance value of sensor capacitance Cm determine the time for the voltage over the capacitor Cm to reach the very accurate and stable upper and lower thresholds, respectively, of the Schmitt trigger input of the integrated circuit U1 determine the oscillation frequency of this astable circuit. The medium 300 dependent capacitor Cm has in embodiments of the invention typically a further capacitor C1 connected in parallel, which could be provided by a stray capacitance between the housing 105, or other conductive parts in its proximity which in the drawing of FIG. 1 has been illustrated by an electrical earth symbol. Advantageously, a separate capacitor C1 is provided, in order to provide better control of that value, so as to provide an oscillation frequency of the astable relaxation oscillator 210 which is in a range from about 2 MHz to about 100 MHz. In respect of the present invention, it has been found that for probes comprising embodiments of the sensor apparatus of the present invention using an advantageous monolithic integrated silicon-on-sapphire AHC (advanced high speed CMOS) Schmitt trigger input integrated inverter or NAND gate circuit, adjusting values of R1 and C1 for the relaxation oscillator to operate at a frequency in the range from about 20 MHz to about 30 MHz has proven to provide a surprisingly highly stable oscillator frequency output as a function of electrical permittivity of the medium 300 on the high pressure side, over a wide range of temperatures, i.e. from room temperature up to temperatures in a range from 200 to 300 degrees C. It has been found that accuracy and stability of the capacitance sensor comprising the relaxation oscillator using a monolithic integrated silicon-on-sapphire AHC (advanced high speed CMOS) Schmitt trigger input integrated inverter or NAND gate circuit, is further enhanced significantly by providing an ultra-stable electrical power supply 250 for feeding the integrated Schmitt trigger circuit with a supply voltage that is stable to within 3 ppm. In advantageous embodiments of the present invention, the elements R1 and U1, and, optionally, C1, are mounted on a common miniature circuit board connected by a short wire 120 the electrode 115 of the capacitive sensor 100, so as to keep the elements of the relaxation oscillator thermally well coupled to each other. The miniature circuit board is advantageously arranged on and attached to an end part of the capacitive sensor sub assembly 100.

In FIG. 1 is also illustrated the provision of a further relaxation oscillator 220, formed by at least a temperature stable capacitor C2, a Schmitt trigger input integrated inverter or NAND gate circuit having its input connected to the temperature stable capacitor C2, and a temperature dependent feedback resistor R4 connected between the input of the integrated Schmitt trigger circuit and its inverted output, providing astable operation at a temperature dependent frequency of oscillation. The further relaxation oscillator 220 is advantageously also arranged on the same miniature circuit board as the media dependent relaxation oscillator 210, to provide on its output a frequency readable to a processor U5 for use by the processor to provide a temperature compensating processing of an output of from the media 300 dependent relaxation oscillator 210. Advantageously, the same miniature circuit board is also providing a first I/O (input/output) circuit U3 for providing a digital indication of the medium 300 dependent oscillation frequency of the Schmitt trigger input integrated circuit relaxation oscillator 210. Advantageously, the same miniature circuit board is also providing a second I/O (input/output) circuit U4 for providing a digital indication of the temperature dependent oscillation frequency of the Schmitt trigger input integrated circuit relaxation oscillator 220. Additional resistor R2 and R3 shown in FIG. 1 are optional, and may be included for advantageously controlling the precision, accuracy, dynamic range, or resolution, at which temperature is to determined by way of the oscillation frequency of the relaxation oscillator 220. Advantageously, the Schmitt trigger input integrated inverter or NAND gate circuits employed for both relaxation oscillators 210 and 220 are provided by a single chip integrated monolithic silicon-on-sapphire integrated advanced high-speed CMOS (AHC).

The electrode 115 could be plate shaped, which is connected to an oscillator circuit 210. The impedance and frequency characteristic of the oscillator circuit are also influenced by both the geometry of the sensor sub assembly and circuit board design, and the surrounding medium. This is being exploited to determine the dielectric constant, permittivity, of the medium 300 which surrounds or is close to the electrode 115. It is also disclosed that the circuit contains a temperature sensitive resistor R4.

Figure 2:
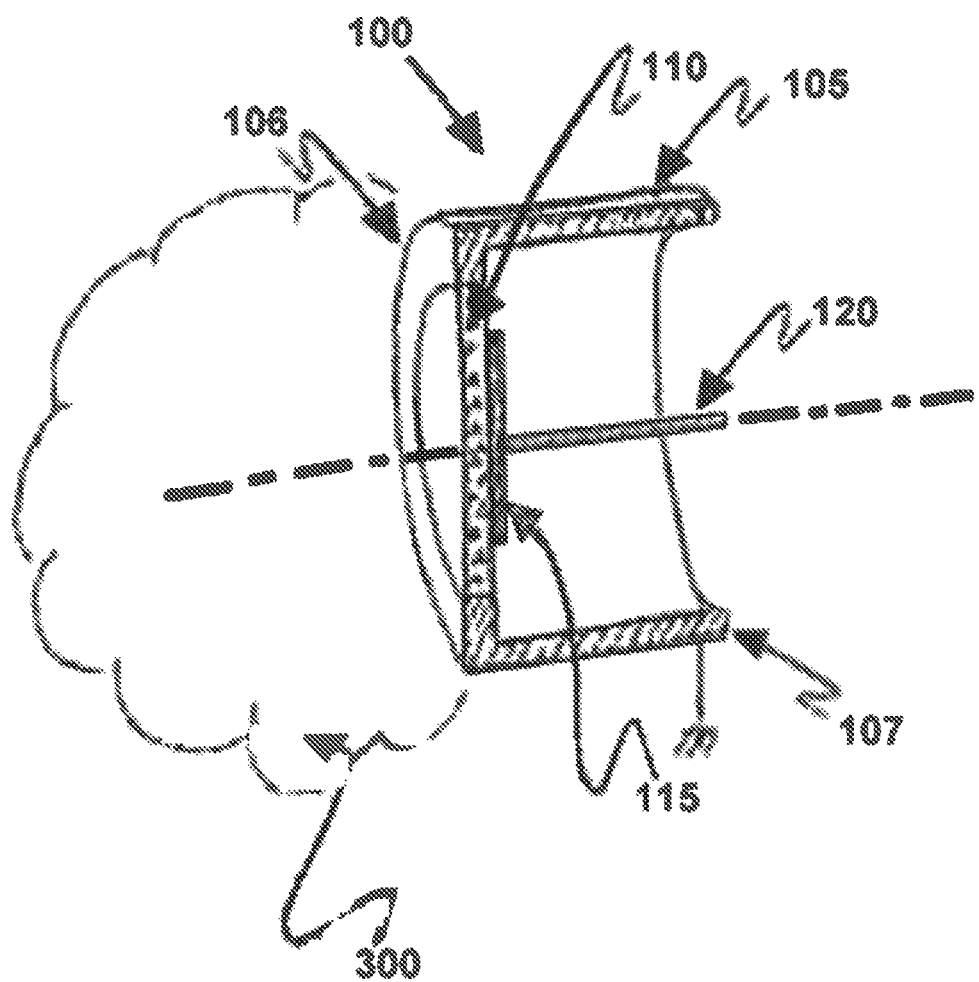
FIG. 2 is a cross section view illustrating a part of a sensor device sub assembly adapted for an embodiment of the present invention.

The nomenclature is otherwise like what it according to common practice may be indicated in electrical circuits. FIG. 2 shows in a schematic representation main features of a physical sensor sub assembly arrangement wherein the invention may put to use. In the cross section view in FIG. 2, details illustrated of the sub assembly of the sensor 100 are the cylindrical housing 105, the housing "front" part 106 to which the dielectric window 110 is sealingly attached at its circumference, the plate shaped electrode 115 being arranged on the "inwards" side of the dielectric window 110, the metal rod or wire 120 connected to a central part of the "inward" face of the electrode 115 for connecting the electrode 115 to the input of the Schmitt trigger input AHC integrated silicon-on-sapphire inverter or gate circuit, and the "rear" part 107 of the cylindrical housing 105 on which there is an arrangement for attaching the common miniature circuit board onto which at least the media 300 dependent relaxation oscillator 210 is amounted. The centrally drawn broken line indicates a central axis of the circular cylindrical shape of the sensor housing 105, hence also a line in the cross section plane of the view of FIG. 2. The arrangement comprises a pressure proof vessel 105 in which a ceramic window 110 has been installed. On the window has been placed an electrode 115 which is connected to an oscillator 210 which is further collocated with a temperature detecting element R4 which in turn is connected with an analog-to-digital converter. A connection from the electronic elements of the sensor arranged in a pressure proof container would as ordinary be a cable connection to a penetrator device (not shown) from which a connection is arranged to a display and control unit (not shown). The window 105 will be in close contact with the medium 300, the properties of which are to be measured.

Figure 3:
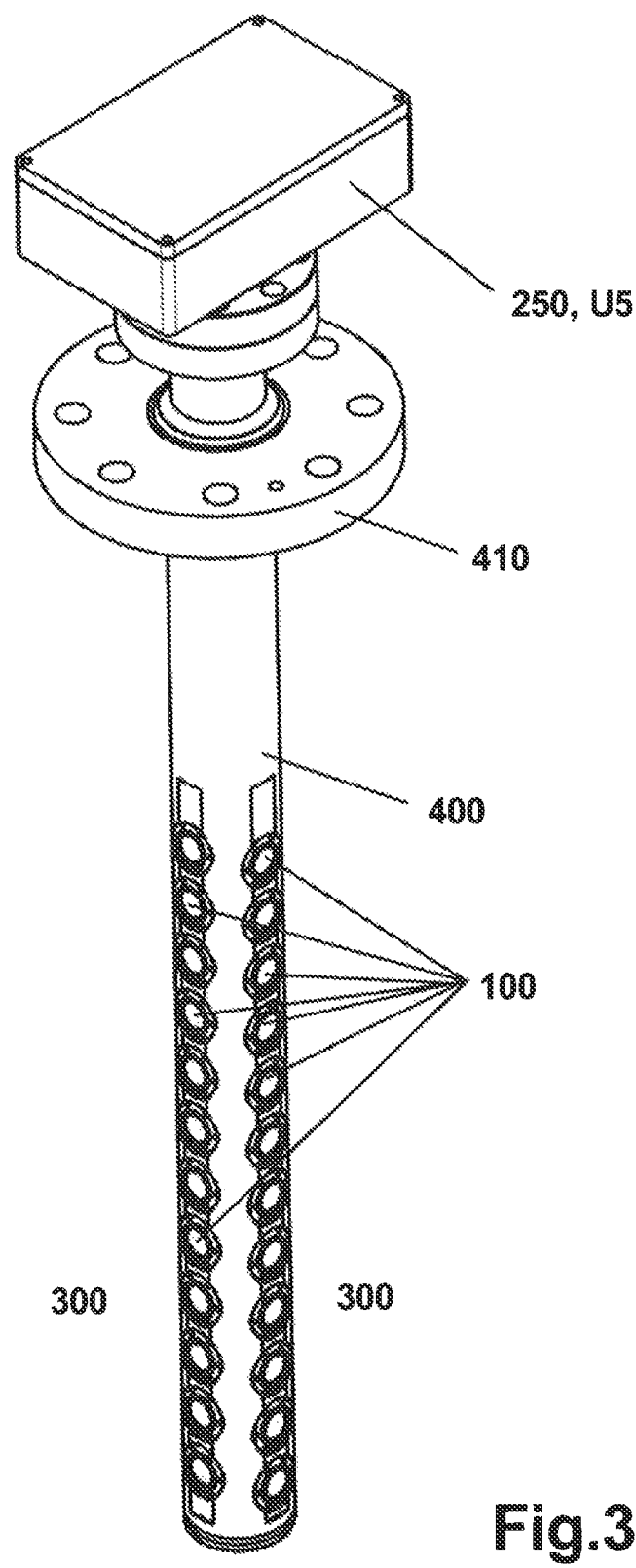
FIG. 3 is a perspective view illustration of a probe device comprising a plurality of embodiments of the sensor device of the present invention.

FIG. 3 shows in a perspective view one of several possible arrangements of a plurality of the Schmitt trigger relaxation oscillator based sensors in a "profiler" probe for determining a profile of a multi-phase medium in a tank, comprising a longitudinal probe housing with a probe housing wall 400 to be positioned vertically in a pressure tank, a plurality of sensors 100 according to the invention in two vertical rows of 12 sensors each in a staggered arrangement for providing a ½ sensor vertical spacing resolution in sensing characteristics of a medium 300 located at the face of each sensor 100 window, a flange 410 for attaching the probe sealingly to a wall of the pressure tank, and an external housing for accommodating electronics and other means that need not be co-located with each sensor device 100, such as the ultra-stable electronic power supply for the integrated advanced high-speed CMOS electronic Schmitt trigger circuit relaxation oscillator 210 and the processor for processing measurements made by each sensor device 100 of the probe.

The invention resides in an improvement of known art in that the oscillator is made significantly less sensitive to noise by it being provided with a Schmitt trigger. Thereby achievable measurement accuracy is improved and calibration is simplified.

The stability of the integrated advanced high-speed CMOS electronic Schmitt trigger circuit relaxation oscillator based sensor according is further improved by combining it with the ultra-stable power supply, advantageously accommodated in a housing located separate from the sensor device.

The invention claimed is:

1. An apparatus for determining a value of a parameter related to electrical permittivity of a fluid media or a composition of fluid media to be characterized in a first container, comprising:

an electronic sensor comprising a first electrical capacitor formed by at least one electrode on a first side of a dielectric barrier and at least a first part of an electrically conducting housing surrounding at least a circumference part of the dielectric barrier and being sealingly attached thereto, the housing configured to be sealingly attached to a wall of one of the first container or a second container so as to allow the fluid media or the composition of fluid media to be configured to occupy a space between the first part of the housing and a second side of the dielectric barrier opposite to the first side, and an electronic relaxation type first oscillator circuit arranged on a first miniature circuit board fitted to the housing and connected with the first electrical capacitor, an electrical power supply connected to the first oscillator circuit and configured to supply electrical power to the first oscillator, and a first frequency measuring device coupled to the first oscillator circuit for providing a measured first oscillator frequency representing the electrical permittivity, wherein the first oscillator circuit is configured to oscillate at the first oscillator frequency dependent on an electrical capacitance of the first electrical capacitor and an electrical resistance of a first electrical resistor, wherein the first oscillator circuit includes an electronic inverter circuit formed by a first integrated advanced high-speed CMOS electronic Schmitt trigger circuit, and wherein the electrical power supply comprises an ultra-stable electrical power supply configured to supply electrical power to the first oscillator circuit at an ultra-stable supply voltage.

2. The apparatus of claim 1, wherein the electronic inverter circuit included in the first oscillator circuit is formed by a NAND gate having one gate output connected to a first terminal of the first electrical resistor and at least two gate inputs whereof a first gate input is connected to the electrode of the first electrical capacitor and a second terminal of the first electrical resistor.

3. The apparatus of claim 2, wherein a second one of the at least two gate inputs is connected to an electrical control line so as to provide a start/stop input of the first oscillator circuit.

4. The apparatus of claim 1, wherein the electrical resistance of the first electrical resistor is selected for the first oscillator frequency to be in a range from about 2 MHz to 100 MHz.

5. The apparatus of claim 4, wherein the electrical resistance of the first electrical resistor is selected for the first oscillator frequency to be in a range from about 10 MHz to 20 MHz.

6. The apparatus of claim 1, wherein the first integrated advanced high-speed CMOS electronic Schmitt trigger circuit is part of a miniature surface mount integrated circuit.

7. The apparatus of claim 6, wherein the first integrated advanced high-speed CMOS electronic Schmitt trigger circuit comprises a monolithic-silicon-on-sapphire integrated circuit.

8. The apparatus of claim 6, wherein the first integrated advanced high-speed CMOS electronic Schmitt trigger circuit contains a plurality of integrated advanced high-speed CMOS electronic Schmitt trigger circuits, and a second circuit from the plurality of integrated advanced high-speed CMOS electronic Schmitt trigger circuits is connected to a temperature stable second electrical capacitor and a temperature sensitive second electrical resistor to form a relaxation type second oscillator circuit configured to oscillate at a second oscillator frequency dependent on a temperature stable electrical capacitance of the second electrical capacitor and a temperature dependent electrical resistance of the second electrical resistor, and the apparatus further comprising a second frequency measuring device coupled to the second oscillator circuit for providing a measured second oscillator frequency representing a temperature of the apparatus, and a temperature compensating means configured to modify the measured first oscillator frequency representing the electrical permittivity in response to the measured second oscillator frequency.

9. The apparatus of claim 1, wherein the housing comprises a thick walled, hollow cylindrical housing with a substantially circular cross section, the dielectric barrier is positioned to seal off a first end of the cylindrical housing, the first miniature circuit board is positioned on the second end of the cylindrical housing, and the at least one first electrode is connected to the first oscillator circuit on the first miniature circuit board by a substantially straight electrical conductor positioned centrally in the cylindrical housing.

10. The apparatus of claim 1, wherein the dielectric barrier comprises a ceramic substrate sealingly brazed at to the housing at the circumference part.

11. A method for determining a value of a parameter related to electrical permittivity of a fluid media or a composition of fluid media to be characterized in a first container, comprising:

providing an electronic sensor comprising a first electrical capacitor formed by at least one electrode on a first side of a dielectric barrier and at least a first part of an electrically conducting housing surrounding at least a circumference part of the dielectric barrier and being sealingly attached thereto, the housing configured to sealingly attach to a wall of one of the first container or a second container so as to allow the fluid media or the composition of fluid media to be configured to occupy a space between the first part of the housing and a second side of the dielectric barrier opposite to the first side, and an electronic relaxation type first oscillator circuit arranged on a first miniature circuit board fitted to the housing and connected with the first electrical capacitor, providing an electrical power supply connected to the first oscillator circuit and configured to supply electrical power to the first oscillator, providing a first frequency measuring device coupled to the first oscillator circuit for providing a measured first oscillator frequency representing the electrical permittivity, arranging the first oscillator circuit to oscillate at the first oscillator frequency dependent on an electrical capacitance of the first electrical capacitor and an electrical resistance of a first electrical resistor, including in the first oscillator circuit an electronic inverter circuit formed by a first integrated advanced high-speed CMOS electronic Schmitt trigger circuit, and adapting the electrical power supply to supply electrical power to the first oscillator circuit at an ultra-stable supply voltage.

12. The method of claim 11, further comprising forming the electronic inverter circuit included in the first oscillator circuit by a NAND gate having one gate output connected to a first terminal of the first electrical resistor and at least two gate inputs whereof a first gate input is connected to the electrode of the first electrical capacitor and a second terminal of the first electrical resistor.

13. The method of claim 12, further comprising connecting a second one of the at least two gate inputs to an electrical control line so as to provide a start/stop input of the first oscillator circuit.

14. The method of claim 11, further comprising selecting the electrical resistance of the first electrical resistor for the first oscillator frequency to be in a range from about 2 MHz to 100 MHz.

15. The method of claim 14, further comprising selecting the electrical resistance of the first electrical resistor for the first oscillator frequency to be in a range from about 10 MHz to 20 MHz.

16. The method of claim 11, further comprising making a first integrated advanced high-speed CMOS electronic Schmitt trigger circuit part of a miniature surface mount integrated circuit.

17. The method of claim 16, further comprising selecting the first integrated advanced high-speed CMOS electronic Schmitt trigger circuit to be a monolithic-silicon-on-sapphire integrated circuit.

18. The method of claim 16, further comprising selecting the first integrated advanced high-speed CMOS electronic Schmitt trigger circuit from a plurality of integrated advanced high-speed CMOS electronic Schmitt trigger circuits, and connecting a second circuit from the plurality of integrated advanced high-speed CMOS electronic Schmitt trigger circuits to a temperature stable second electrical capacitor and a temperature sensitive second electrical resistor to form a relaxation type second oscillator circuit configured to oscillate at a second oscillator frequency dependent on a temperature stable electrical capacitance of the second electrical capacitor and a temperature dependent electrical resistance of the second electrical resistor, and the method further comprising coupling a second frequency measuring device to the second oscillator circuit for providing a measured second oscillator frequency representing a temperature of the apparatus, and providing a temperature compensating means configured to modify the measured first oscillator frequency representing the electrical permittivity in response to the measured second oscillator frequency.

19. The method of claim 11, further comprising providing the housing comprises a thick walled, hollow cylindrical housing with a substantially circular cross section, positioning the dielectric barrier to seal off a first end of the cylindrical housing, positioning the first miniature circuit board on the second end of the cylindrical housing, and connecting the at least one first electrode to the first oscillator circuit on the first miniature circuit board by a substantially straight electrical conductor positioned centrally in the cylindrical housing.

20. The method of claim 11, further comprising providing the dielectric barrier by ceramic substrate sealingly brazed at to the housing at the circumference part.

* * * * *